United States Patent

Kamagata et al.

Patent Number: 4,658,009
Date of Patent: Apr. 14, 1987

[54] NOVEL 2-SUBSTITUTED-4,6-DIAMINO-S-TRIAZINE/ISOCYANURIC ACID ADDUCT, PROCESS FOR SYNTHESIS OF SAID ADDUCT AND PROCESS FOR CURING POLYEPOXY RESIN WITH SAID ADDUCT

[75] Inventors: Kazuo Kamagata; Toshiaki Yamada, both of Saitama; Natsuo Sawa, Kagawa, all of Japan

[73] Assignee: Shikoku Chemicals Corporation, Kagawa, Japan

[21] Appl. No.: 839,189

[22] Filed: Mar. 13, 1986

[30] Foreign Application Priority Data

Mar. 14, 1985 [JP] Japan .................. 60-51828

[51] Int. Cl.⁴ .................. C08G 59/50; C07D 403/00
[52] U.S. Cl. .................. 528/109; 525/504; 528/111; 528/118; 528/365; 528/367; 544/205; 544/206; 544/207
[58] Field of Search .................. 528/111, 118, 367, 109, 528/365; 544/205, 206, 207

[56] References Cited

U.S. PATENT DOCUMENTS

| 4,189,577 | 2/1980 | Sawa et al. | 528/118 X |
| 4,205,156 | 5/1980 | Sawa et al. | 528/118 X |
| 4,555,532 | 11/1985 | Tanaka et al. | 528/118 X |
| 4,567,259 | 1/1986 | Sawa et al. | 544/207 |
| 4,593,069 | 6/1986 | Kamagata et al. | 528/118 X |

Primary Examiner—Earl Nielsen
Attorney, Agent, or Firm—Sherman and Shalloway

[57] ABSTRACT

Disclosed is a 2-substituted-4,6-diamino-s-triazine/isocyanuric acid adduct represented by the following formula:

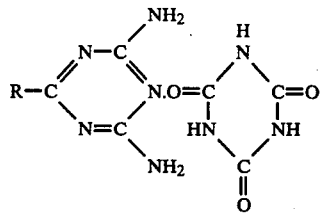

wherein R stands for an alkyl group having 2 to 20 carbon atoms, an unsubstituted or cyano group-substituted aryl group, or a group of the formula $R^1$—$CH_2CH_2$— in which $R^1$ stands for an alkoxy group having up to 20 carbon atoms, an acyloxy group, an amino group, an N-substituted amino group, a benzotriazolyl group or a 2-alkylimidazolyl-(4)-dithiocarbonyl group, or by the following formula:

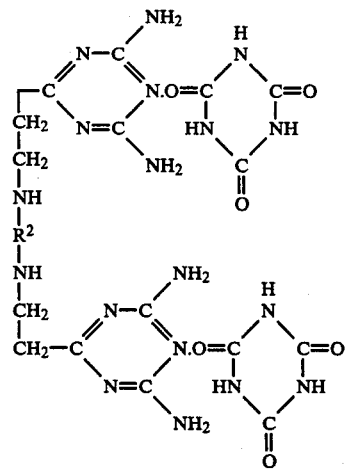

wherein $R^2$ stands for an alkylene group which may have an intervening imino or phenylene group.

When this adduct is used for curing a polyepoxy resin, a cured product having good heat resistance, insulating property and adhesion and an excellent migration-preventing effect is formed.

43 Claims, No Drawings

NOVEL 2-SUBSTITUTED-4,6-DIAMINO-S-TRIAZINE/ISOCYANURIC ACID ADDUCT, PROCESS FOR SYNTHESIS OF SAID ADDUCT AND PROCESS FOR CURING POLYEPOXY RESIN WITH SAID ADDUCT

BACKGROUND OF THE INVENTION (1) Field of the Invention

The present invention relates to a novel 2-substituted-4,6-diamino-s-triazine/isocyanuric acid adduct (hereinafter referred to as "adduct"), a process for the synthesis of this adduct and a process for curing a polyepoxy resin with this adduct.

Since an epoxy resin cured by using the adduct of the present invention exerts a prominent effect of preventing the migration of metals forming a wiring circuit, such as gold, silver and copper, it is expected that the present invention is especially valuable in the fields of the production of sealing materials for electronic parts, copper-lined laminates and coating materials for organic and inorganic substrates.

(2) Description of the Prior Art

Epoxy resins have been widely used as sealing materials, insulating materials and matrix materials for substrates in the fields of electronic parts and printed circuit boards, because they are excellent in the heat resistance, electrically insulating property and adhesiveness.

However, epoxy resins are poor in the function of preventing the migration, that is, the phenomenon in which a metal constituting a wire or electrode on an insulating material is caused to migrate on the insulating material by the potential difference in a high-humidity atmosphere, and therefore, such troubles as insufficient insulation and formation of short circuits readily occur.

With recent reduction of the size and recent increase of the density in electronic parts and also with recent desire to make wiring circuits finer, the requirement for preventing the migration becomes severe.

Various commercially available migration-preventing resins are still insufficient because curing conditions are severe, the shrinkage by curing is extreme or the adhesiveness is low.

Glass frits used for ceramic substrates have an excellent migration-preventing effect, but they are defective in that they are expensive and the baking temperature is high.

SUMMARY OF THE INVENTION

Under this background, we made research, and as the result, it was found that if a 2-substituted-4,6-diamino-s-triazine/isocyanuric acid adduct represented by the following formula is added as an indispensable component to a polyepoxy resin, a cured product having good heat resistance, insulating property and adhesion and an excellent migration-preventing action is formed:

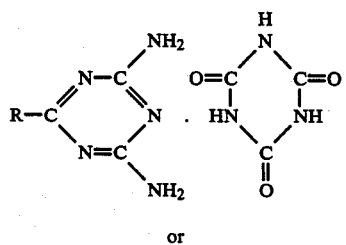

or

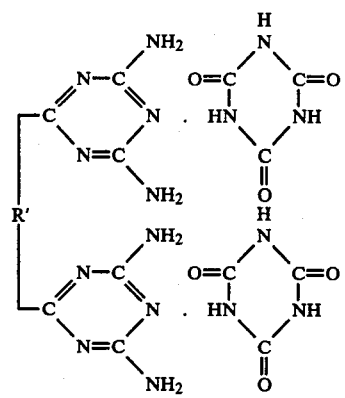

wherein R stands for an ethyl group, an n-propyl group, an n-heptadecyl group, a methoxyethyl group, an n-propoxyethyl group, an isopropoxyethyl group, an n-butoxyethyl group, an n-octadecyloxyethyl group, an aminoethyl group, an allylaminoethyl group, an n-propylaminoethyl group, an n-dodecylaminoethyl group, a β-aminoethylaminoethyl group, an o-cyanophenyl group, an m-cyanophenyl group, a p-cyanophenyl group, a phenylaminoethyl group, an o-toluylaminoethyl group, an m-toluylaminoethyl group, a p-toluylaminoethyl group, a β-naphthylaminobenzyl group, an acetoxyethyl group, an acryloyloxyethyl group, a methacryloyloxyethyl group, a 2-ethylimidazolyl-(4)-dithiocarbonylethyl group, a β-pyridylaminoethyl group or a 2-benzotriazolylethyl group, and R' stands for a bis-(diethylenetriamino-1,3)-ethyl group or a bis-(m-xylylenediamino)ethyl group. We have now completed the present invention based on this finding.

The adduct of the present invention represented by the above formula can be easily obtained by heating and dissolving a corresponding 2-substituted-4,6-diamino-s-triazine compound and isocyanuric acid in the presence of water, cooling the reaction mixture, recovering the precipitated crystal by filtration and drying the crystal.

DETAILED DESCRIPTION OF THE PREFERRED EMBODIMENTS

The 2-substituted-4,6-diamino-s-triazine used as the starting material of the adduct of the present invention is a compound obtained by reacting a nitrile with dicyandiamide according to a known method (see, for example, S. Birtwell, J.C.S., 1952, 1279). Furthermore, this starting material can be obtained by a novel addition reaction of 2-vinyl-4,6-diamino-s-triazine (C. G. Overgerger et al. J.A.C.S., 80, 988 (1958)), which is obtained by reaction of a biguanide with acrylic acid chloride, with an active hydrogen-containing alcohol, amine or carboxylic acid.

The adduct of the present invention can be easily synthesized by completely dissolving the above-mentioned starting material and an equimolar or substantially equimolar amount of isocyanuric acid in hot water, cooling the reaction mixture, recovering the precipitated crystal by filtration and drying the crystal.

Properties of specific examples of the adduct of the present invention will now be described.

Incidentally, in each of the structural formulae given hereinafter, A indicates

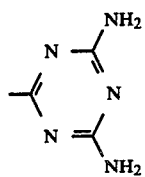

and ICA indicates

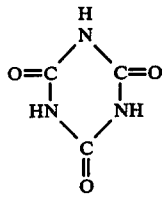

(isocyanuric acid). Each parenthesized value in $v_{cm^{-1}}^{KBr}$ indicates the transmittance (%), and Rf indicates a TLC value (silica gel, developed by ethanol, colored by iodine).

(1) 2-Ethyl-4,6-diamino-s-triazine/isocyanuric acid adduct
Structural formula: $CH_3CH_2$—A/ICA.
State: colorless crystal.
Melting point: 364° C.
$v_{cm^{-1}}^{KBr}$: 3420(11), 3350(19), 3250(17), 3000(25), 2800(21), 1770(7), 1710 (4), 1650(10), 1540 (6), 1425 (7), 1405(23), 1235(44), 1060(41), 1020(46), 890(47), 820(53), 760(27).

(2) 2-n-Propyl-4,6-diamino-s-triazine/isocyanuric acid adduct
Structural formula: $CH_3CH_2CH_2$—A/ICA.
State: colorless crystal.
Melting point: 220° C. (decomposition).
Rf: 0.70–0.80, 0.00.
$v_{cm^{-1}}^{KBr}$: 3400(17), 3340(22), 3230(18), 3085(29), 3020(29), 2960(29), 2870(37), 2800(30), 2530(43), 2140(66), 1773(10), 1730 (6), 1688 (1), 1650(14), 1632(11), 1532 (7), 1453(12), 1438(12), 1410(10), 1255(59), 1212(58), 1152(61), 1120(63), 1067(43), 1035(57), 1000(57), 887(50), 810(49), 760(31).

(3) 2-Heptadecyl-4,6-diamino-s-triazine/isocyanuric acid adduct
Structural formula: $n-C_{17}H_{35}$—A/ICA.
State: colorless crystal.
Melting point: 209° C. (decomposition).
Rf: 0.0, 0.4–0.6.
$v_{cm^{-1}}^{KBr}$: 3400(40), 3340(41), 3230(43), 3010(48), 2920(27), 2850(33), 2765(47), 2515(57), 1765(34), 1713(22), 1665(43), 1650(39), 1542(28), 1465(43), 1435(33), 1398(46), 1115(78), 1063(69), 1010(76), 890(75).

(4) 2-Methoxyethyl-4,6-diamino-s-triazine/isocyanuric acid adduct
Structural formula: $CH_3O-CH_2CH_2$—A/ICA.
State: colorless crystal, neutral.
Rf: 0.0 (ICA), 0.5–0.6 (corresponding to triazine).
$v_{cm^{-1}}^{KBr}$: 3440(11), 3380(15), 3330(19), 3230(14), 2740(19), 2540(32), 1775(11), 1710 (1), 1640 (6), 1540 (1), 1450 (8), 1420 (2), 1380(19), 1315(35), 1215(36), 1095(22), 1080(14), 1060(33), 1015(35), 900(45), 800(38), 760(28).

(5) 2-n-Propoxyethyl-4,6-diamino-s-triazine/isocyanuric acid adduct
Structural formula: $CH_3CH_2CH_2OCH_2CH_2$—A/ICA.
Melting point: higher than 250° C.
Rf: 0.0, 0.45–0.55.
$v_{cm^{-1}}^{KBr}$: 3450(32), 3350(32), 3245(36), 3030(40), 2965(44), 2880(48), 2785(42), 2335(68), 1768(29), 1720(13), 1685(35), 1630(20).

(6) 2-Isopropoxyethyl-4,6-diamino-s-triazine/isocyanuric acid adduct
Structural formula:

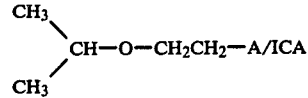

State: colorless crystal.
Melting point: higher than 250° C.
Rf: 0.0, 0.55–0.70.
$v_{cm^{-1}}^{KBr}$: 3445(35), 3345(25), 3235(32), 3140(38), 3023(39), 2970(40), 2783(37), 1763(16), 1718(13), 1682(18), 1663(21), 1625(21), 1540(11), 1450(16), 1430(14), 1355(47), 1337(48), 1273(55), 1201(53), 1168(59), 1140(58), 1120(57), 1060(48), 1010(61), 815(55), 760(41).

(7) 2-n-Butoxyethyl-4,6-diamino-s-triazine/isocyanuric acid adduct
Structural formula: $n-C_4H_9-O-CH_2CH_2$—A/ICA.
State: colorless crystal.
Melting point: higher than 260° C.
Rf: 0.0.
$v_{cm^{-1}}^{KBr}$: 3350(33), 3230(39), 2790(47), 2220(66), 1766(29), 1720(22), 1690(31), 1665(34), 1545(21), 1445(27), 1260(64), 1204(65), 1075(61), 1060(61), 1014(65), 990(65), 816(61), 760(51), 690(66).

(8) 2-n-Octadecyloxyethyl-4,6-diamino-s-triazine/isocyanuric acid adduct
Structural formula: $n-C_{18}H_{37}O-CH_2CH_2$—A/ICA.
State: colorless crystal, neutral.
Melting point: 112° C. (decomposition).
Rf: 0.0.
$v_{cm^{-1}}^{KBr}$: 3340(32), 3210(30), 2920(14), 2850(18), 1765(48), 1715(37), 1685(35), 1645(29), 1540(40), 1465(39), 1395(51), 1240(53), 1190(56), 1110(60), 1055(63), 1045(64), 970(68), 810(71), 790(71), 755(77), 710(78).

(9) 2-Aminoethyl-4,6-diamino-s-triazine/isocyanuric acid adduct
Structural formula: $H_2NCH_2CH_2$—A/ICA.
State: colorless crystal, neutral
Melting point: higher than 250° C.
Rf: 0.0.
$v_{cm^{-1}}^{KBr}$: 3350(35), 3230(36), 2810(46), 1770(38), 1720(22), 1640(30), 1550(26), 1450(36), 1360(49), 1260(60), 1060(60), 785(59), 760(56).

(10) 2-Allylaminoethyl-4,6-diamino-s-triazine/isocyanuric acid adduct
Structural formula: $CH_2=CHCH_2NHCH_2CH_2$—A/ICA.
State: colorless crystal, neutral.
Rf: 0.00–0.05.
$v_{cm^{-1}}^{KBr}$: 3350(29), 3220(37), 2800(50), 1780(43), 1745(33), 1720(32), 1625(33), 1550(22), 1445(35), 1260(61), 995(62), 910(60), 815(60), 800(58), 780(62), 760(53).

(11) 2-Propylaminoethyl-4,6-diamino-s-triazine/isocyanuric acid adduct

Structural formula: $CH_3CH_2CH_2NHCH_2CH_2$—A/ICA.

State: colorless crystal, neutral.
Melting point: higher than 250° C.
Rf: 0.00–0.05.

$\nu_{cm-1}^{KBr}$: 3350(13), 3200(15), 3000(20), 2780(21), 1770(11), 1710 (5), 1630 (8), 1540 (3), 1440 (9), 1355(16), 1245(33), 1060(40), 1000(45), 855(42), 810(43), 810(43), 780(36), 755(32).

(12) 2-n-Dodecylaminoethyl-4,6-diamino-s-triazine/isocyanuric acid adduct

Structural formula: $n-C_{12}H_{25}NHCH_2CH_2$—A/ICA.

State: colorless crystal, neutral.
Melting point: 229° C. (decomposition). Rf: 0.00–0.10.

$\nu_{cm-1}^{KBr}$: 3340(38), 3200(35), 2920(33), 2850(39), 1765(45), 1720(27), 1645(29), 1545(23), 1445(32), 1400(38), 1355(43), 1255(58), 1120(63), 1055(60), 1045(60), 1015(61), 820(57), 780(53), 755(59).

(13) 2-Octadecylaminoethyl-4,6-diamino-s-triazine/isocyanuric acid adduct

Structural formula: $n-C_{18}H_{37}NHCH_2CH_2$—A/ICA.

State: colorless crystal, neutral.
Melting point: 222° C. (decomposition).
Rf: 0.00–0.10.

$\nu_{cm-1}^{KBr}$: 3430(44), 3350(44), 3200(45), 2920(34), 2840(38), 1765(53), 1710(33), 1620(35), 1545(34), 1465(47), 1430(43), 1360(43), 1015(67), 810(66), 780(58), 755(66), 705(69).

(14) 2-Aminoethylaminoethyl-4,6-diamino-s-triazine/isocyanuric acid adduct

Structural formula: $H_2NCH_2CH_2NHCH_2CH_2$—A/ICA.

State: colorless crystal, slightly basic.
Melting point: 247° C. (decomposition).
Rf: 0.0.

$\nu_{cm-1}^{KBr}$: 3330(24), 3150(24), 2800(35), 1765(40), 1720(13), 1610(12), 1550(15), 1440(27), 1410(29), 1360(28), 1255(53), 1080(57), 1010(58), 800(51), 780(44), 760(53).

(15) 2-o-Cyanophenyl-4,6-diamino-s-triazine/isocyanuric acid adduct

Structural formula:

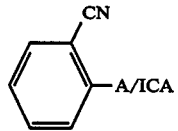

Melting point: higher than 270° C.
Rf: 0.0.

$\nu_{cm-1}^{KBr}$: 3472(42), 3390(46), 3350(45), 3220(45), 3060(47), 2800(57), 2238(59), 1772(22), 1726(22), 1674(53), 1635(32), 1586(51), 1560(29), 1520(62), 1460(38), 1410(40), 1396(58), 1300(77), 1274(73), 1266(76), 1194(78), 1102(80), 1070(73), 1048(75), 985(82), 908(77), 810(71), 768(69), 748(46), 680(90).

(16) 2-m-Cyanophenyl-4,6-diamino-s-triazine/isocyanuric acid adduct

Structural formula:

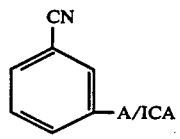

State: colorless crystal, neutral.
Melting point: higher than 250° C.
Rf: 0.0.

$\nu_{cm-1}^{KBr}$: 3436(25), 3360(24), 3240(22), 3080(25), 2840(50), 27 (50), 2690(53), 2250(36), 1774 (8), 1750(13), 1730 (4), 1679(33), 1652(13), 1602(46), 1563(12), 1532(15), 1456(14), 1422(29), 1404(27), 1386(34), 1303(83), 1250(70), 1220(84), 1170(85), 1131(89), 1090(86), 1072(70), 1054(73), 998(89), 980(90), 940(85), 922(71), 910(76), 822(77), 798(37), 770(81), 752(43), 726(68), 670(75).

(17) 2-p-Cyanophenyl-4,6-diamino-s-triazine/isocyanuric acid adduct

Structural formula:

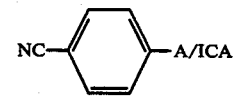

State: colorless crystal, neutral.
Melting point: higher than 250° C.
Rf: 0.00–0.10, 0.20–0.30.

$\nu_{cm-1}^{KBr}$: 3420(37), 3350(35), 3240(33), 3070(39), 2240(36), 1770(13), 1725(10), 1670(31), 1645(17), 1560(13), 1525(25), 1450(17), 1420(33), 1400(27), 1385(27), 1065(53), 1050(52), 900(15), 855(54), 800(38), 745(41).

(18) 2-Phenylaminoethyl-4,6-diamino-s-triazine/isocyanuric acid adduct

Structural formula:

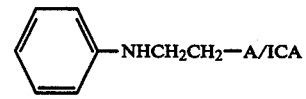

State: colorless crystal, neutral.
Melting point: 242° C. (decomposition).
Rf: 0.00–0.10, 0.65–0.80.

$\nu_{cm-1}^{KBr}$: 3460(33), 3350(37), 3240(37), 3020(45), 2800(45), 1770(39), 1715(13), 1625(14), 1550(20), 1495(46), 1450(32), 1430(27), 1270(64), 1245(64), 1080(59), 1010(64), 885(62), 805(65), 760(50), 690(59).

(19) 2-o-Toluylaminoethyl-4,6-diamino-s-triazine/isocyanuric acid adduct

Structural formula

State: colorless crystal, neutral, soluble in hot methanol.
Melting point: higher than 250° C.
Rf: 0.35–.052.

$\nu_{cm^{-1}}^{KBr}$: 3440(17), 3340(18), 3240(18), 3020(23), 2710(24), 1770(13), 1720 (1), 1622 (1), 1550 (4), 1500(21), 1445 (8), 1425 (7), 1300(54), 1265(46), 1250(45), 1205(52), 1120(53), 1075(45), 1008(56), 880(52), 805(54), 761(31).

(20) 2-m-Toluylaminoethyl-4,6-diamino-s-triazine/isocyanuric acid adduct

Structural formula

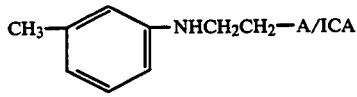

State: colorless crystal.
Melting point: 225° C. (decomposition).
Rf: 0.0, 0.35–0.55.

$\nu_{cm^{-1}}^{KBr}$: 3340(32), 3230(37), 3020(43), 2780(43), 1765(28), 1715(13), 1625(23), 1547(15), 1435(20), 1400(35), 1320(53), 1268(54), 1170(57), 1060(58), 988(59), 880(59), 811(60), 758(46), 680(65).

(21) 2-p-Toluylaminoethyl-4,6-diamino-s-triazine/isocyanuric acid adduct

Structural formula:

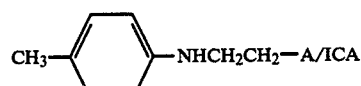

State: colorless crystal.
Melting point: 225° C. (decomposition).
Rf: 0.00, 0.20–0.50.

$\nu_{cm^{-1}}^{KBr}$: 3365(22), 3233(27), 3025(35), 2785(36), 1768(24), 1718(10), 1683(27), 1630(16), 1550(10), 1518(20), 1440(15), 1320(51), 1298(54), 1258(49), 1183(57), 1123(56), 1068(52), 1010(56), 883(58), 808(45), 762(43), 691(61).

(22) 2-Benzylaminoethyl-4,6-diamino-s-triazine/isocyanuric acid adduct

Structural formula

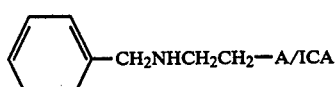

State: colorless crystal.
Melting point: higher than 250° C.
Rf: 0.00, 0.00–0.15.

$\nu_{cm^{-1}}^{KBr}$: 3330(25), 3200(26), 2780(37), 1760(30), 1717(14), 1623(14), 1540(9), 1440(18), 1400(25), 1350(27), 1243(51), 1200(54), 1175(55), 1105(62), 1052(59), 973(58), 848(58), 810(51), 780(48), 752(49), 737(52), 685(50).

(23) 2-β-Naphthylaminoethyl-4,6-diamino-s-triazine/isocyanuric acid adduct

Structural formula:

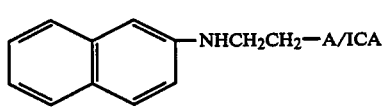

State: colorless crystal.
Melting point: 210° C. (decomposition).

Rf: 0.00, 0.40–0.50.

$\nu_{cm^{-1}}^{KBr}$: 3475(48), 3400(40), 3340(42), 3200(46), 3090(43), 2800(51), 1770(45), 1729(28), 1708(24), 1655(34), 1630(29), 1600(43), 1548(15), 1520(32), 1485(44), 1445(23), 1400(42), 1357(51), 1303(58), 1275(58), 1261(59), 1223(58), 1182(59), 1156(66), 1143(66), 1123(66), 1098(67), 1065(64), 1013(63), 985(67), 905(65), 860(65), 810(51), 758(56), 738(60).

(24) 2-Acetoxyethyl-4,6-diamino-s-triazine/isocyanuric acid adduct

Structural formula: $CH_3COOCH_2CH_2$—A/ICA.
State: colorless crystal, neutral.
Melting point: higher than 250° C.
Rf: 0.0.

$\nu_{cm^{-1}}^{KBr}$: 3340(36), 3350(42), 3240(41), 3020(45), 2800(46), 1770(38), 1710(21), 1625(27), 1545(30), 1430(34), 1255(50), 1075(58), 1040(56), 800(64), 760(58).

(25) 2-Acryloyloxyethyl-4,6-diamino-s-triazine/isocyanuric acid adduct

Structural formula: $CH_2{=}CHCOOCH_2CH_2$—A/ICA.
State: colorless crystal, neutral
Melting point: 212° C. (decomposition)
Rf: 0.00, 0.70–0.80.

$\nu_{cm^{-1}}^{KBr}$: 3420(23), 3350(22), 3240(23), 3020(32), 2800(30), 1770(15), 1720(4), 1630(13), 1545(8), 1440(13), 1260(41), 1190(38), 1060(43), 985(46), 885(51), 825(49), 805(50), 760(41).

(26) 2-Methacryloyloxyethyl-4,6-diamino-s-triazine/isocyanuric acid adduct

Structural formula:

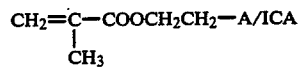

State: colorless crystal, neutral.
Melting point: 178° C. (decomposition).
Rf: 0.00.

$\nu_{cm^{-1}}^{KBr}$: 3370(17), 3230(25), 3020(35), 2780(34), 1765(16), 1715(10), 1680(15), 1655(17), 1540(10), 1445(14), 1430(13), 1400(32), 1355(51), 1200(58), 1165(55), 1060(57), 990(57), 870(61), 820(60), 810(60), 755(38).

(27) 2-(2'-Ethylimidazolyl-(4))-dithiocarbonylethyl-4,6-diamino-s-triazine/isocyanuric acid adduct Structural formula:

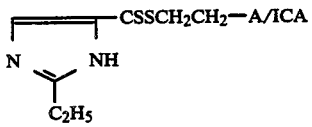

State: yellow crystal, neutral.
Melting point: 198° C. (decomposition).
Rf: 0.00, 0.60–0.70.

$\nu_{cm^{-1}}^{KBr}$: 3530(50), 3445(32), 3320(39), 3250(39), 3080(41), 2810(54), 1770(32), 1725(17), 1715(20), 1680(53), 1640(27), 1545(24), 1520(41), 1455(34), 1435(45), 1425(46), 1405(50), 1260(68), 1115(57), 1080(53), 1050(59), 1010(71), 880(72), 840(66), 810(66), 775(70), 755(56).

(28) 2-β-Pyridylaminoethyl-4,6-diamino-s-triazine/isocyanuric acid adduct

Structural formula:

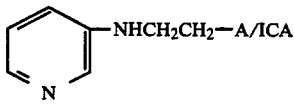

State: colorless crystal, neutral.
Melting point: higher than 250° C.
Rf: 0.00, 0.40–0.50.
$v_{cm-1}{}^{KBr}$: 3340(25), 3220(27), 2810(39), 1770(28), 1720(11), 1630(16), 1600(19), 1545(12), 1440(22), 1355(40), 1190(56), 1065(58), 1000(58), 860(60), 820(58), 780(55), 760(52).

(29) 2-Benzotriazolylethyl-4,6-diamino-s-triazine/isocyanuric acid adduct
Structural formula:

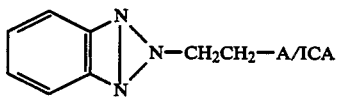

State: colorless crystal, neutral.
Melting point; higher than 250° C.
Rf: 0.00, 0.30–0.40.
$v_{cm-1}{}^{KBr}$: 3390(25), 3340(27), 3210(28), 3020(37), 2800(36), 1770(18) 1715(9), 1690(15), 1655(19), 1540(13), 1445(15), 1410(25), 1325(55), 1280(55), 1265(56), 1215(53), 1080(59), 1055(53), 1005(60), 910(60), 810(60), 755(38), 745(46), 735(50).

(30) 2-(Bis-1',3'-diethylene-triaminoethyl)-4,6-diamino-s-triazine/isocyanuric acid adduct
Structural formula:

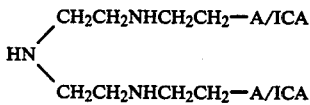

State: colorless crystal.
Melting point: 183° C. (decomposition).
Rf: 0.00.
$v_{cm-1}{}^{KBr}$: 3330(21), 3170(22), 2820(31), 2760(31), 2340(51), 1720(19), 1623(15), 1540(11), 1440(20), 1350(22), 1240(35), 1055(43), 990(43), 810(38), 778(32), 755(39).

(31) 2-(Bis-m-xylylene-diaminoethyl)-4,6-diamino-s-triazine/isocyanuric acid adduct
Structural formula:

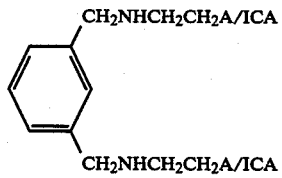

State: colorless crystal, neutral.
Melting point: 238° C. (decomposition).
Rf: 0.00.
$v_{cm-1}{}^{KBr}$: 3340(39), 3180(40), 2820(45), 1735(34), 1715(34), 1630(30), 1600(29), 1540(28), 1480(39), 1440(38), 1410(38), 1380(39), 1350(42), 810(60), 780(53), 755(59), 695(64).

Incidentally, $vcm^{-1}$ of each adduct is different from that of A or that of ICA. This proves that the adduct is not a mere mixture of A and ICA.

Each adduct is decomposed to A and an alkali salt of ICA by an action of an aqueous alkali solution, and a substantially stoichiometric amount of A is recovered as a crystal by filtration (the alkali salt of ICA is transferred to the filtrate). This also proves that the compound of the present invention is an adduct.

An embodiment of the process for the synthesis of the adduct of the present invention will now be described.

A corresponding 2-substituted-4,6-diamino-s-triazine and an equimolar or substantially equimolar amount of isocyanuric acid are heated in water or an aqueous solvent containing a lower alcohol for several minutes to several hours to completely dissolve the reactants, and the reaction mixture is then cooled and the precipitated crystal is recovered by filtration and dried.

It is most preferred that the amount used of the aqueous solvent be such that the reactants are completely dissolved at a temperature close to the boiling point, but this condition is not particularly critical and a smaller amount may be adopted.

Heating may be carried out under pressure, but this heating under pressure is not preferred because the cost is increased When the compound of the present invention is used as a curing agent for a polyepoxy resin, there can be obtained a cured product having good heat resistance, insulating property and adhesiveness and an excellent migration-preventing effect.

In the process for curing a polyepoxy resin according to the present invention, a curing agent or curing promotor, such as an aliphatic amine, an aromatic amine, a tertiary amine, a polyamide resin or an acid anhydride, may be used in combination with the adduct of the present invention. Especially when such an additive and the adduct of the present invention are incorporated in a liquid polyepoxy resin, the storage stability is improved, and curing is accomplished at a lower temperature within a shorter time.

Particularly, if 2,4-diamino-6-(2'-methylimidazolyl-(1'))ethyl-s-triazine, 2,4-diamino-6-(2'-methylimidazolyl-(1'))ethyl-s-triazine/isocyanuric acid adduct, 2-phenyl-4,5-dihydroxymethylimidazole, 2-phenyl-4-methyl-5-hydroxymethylimidazole, 4,4'-methylene-bis-(2-ethyl-5-methylimidazole), 2-phenyl-4-benzyl-5-hydroxymethylimidazole or 2-phenyl-4,5-dibenzylimidazole is used in combination with the adduct of the present invention, a so-called one-pack type composition can be obtained.

When 2-methylimidazole, 2-ethyl-4-methylimidazole, 2-phenylimidazole, 2-undecylimidazole, 2-heptadecylimidazole, 2-phenyl-4-methylimidazole, 1-cyanoethyl-2-methylimidazole, 1-cyanoethyl-2-ethyl-4-methylimidazole, 1-cyanoethyl-2-phenylimidazole, 1-cyanoethyl-2-undecylimidazole, 1-cyanoethyl-2-phenyl-4-methylimidiazole or 1-benzyl-2-methylimidazole is used in combination of the adduct of the present invention, a storage stability required for a one-pack type composition cannot be obtained, but if these ingredients are mixed with a polyepoxy resin just before the application and the mixture is heated, a cured product excellent in the migration-preventing action can be obtained.

The polyepoxy resin used in the present invention contains at least one epoxy group per molecule, and the epoxy group may be

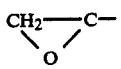

present at the end of the molecule, or it may be

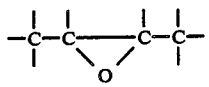

interposed in the midway of the molecule. The polyepoxy compound may be an aliphatic, alicyclic, aromatic or heterocyclic compound. The polyepoxy compound may be substituted with a non-hindering substituent such as a hydroxyl group, an alkyl group, an alkoxy group, an ester group, an acetal group or an ether group.

As typical instances of the polyepoxy resin suitable for carrying out the present invention, there can be mentioned a polyglycidyl ether of a polyhydric phenol, such as a diglycidyl ether of bisphenol A or a diglycidyl ether of bisphenol A, and other epoxidized phenol, a novolak resin, an alicyclic epoxy resin and a brominated epoxy resin thereof.

The adduct should be incorporated in an amount of 5 to 50 parts by weight per 100 parts by weight of the polyepoxy resin, and it is preferred that the curing agent or curing promotor be used in an amount of 0.025 to 10 parts by weight per 100 parts by weight of the polyepoxy resin. If the amounts of these compounds are too large and exceed the above-mentioned ranges, the thermal distortion temperature is reduced, and if the amounts of the additives are too short, a long time is required for curing and the composition is not preferred from the practical viewpoint.

Conditions for curing the polyepoxy resin are changed to some extent according to the kinds of the resin and curing agent and the amount incorporated of the curing agent, but it is ordinarily sufficient if curing is carried out at 100° to 250° C. for 2 to 60 minutes.

The present invention will now be described with reference to the following examples and referential example that by no means limit the scope of the invention.

REFERENTIAL EXAMPLE

This referential example illustrates the synthesis of a 2-substituted-4,6-diamino-s-triazine.

2-Vinyl-4,6-diamino-s-triazine and a substantially equimolar amount of an active hydrogen-containing compound were heated in an aqueous solvent or in the absence of a solvent to effect addition reaction, and the reaction mixture was cooled and the precipitated crystal was recovered by filtration and was dried to obtain a 2-substituted-4,6-diamino-s-triazine having the physical properties shown in Table 1.

Incidentally, Rf in Table 1 indicates a TLC value (silica gel, developed by ethanol, colored by iodine).

TABLE 1

| Active Hydrogen-Containing Compound Used | Synthesized 2-Substituted-4,6-Diamino-s-Triazine | | | |
|---|---|---|---|---|
| | Structural Formula | Melting Point (°C.) | Rf | State |
| $CH_3OH$ | $CH_3OCH_2CH_2A$ | 195–198 | 0.5–0.6 | colorless crystal, neutral |
| $CH_3CH_2CH_2OH$ | $CH_3CH_2CH_2OCH_2CH_2A$ | 165–168 | 0.45–0.55 | " |
| $(CH_3)_2CH{-}OH$ | $(CH_3)_2CH{-}O{-}CH_2CH_2A$ | 175–183 | 0.4–0.55 | " |
| $n\text{-}C_4H_9OH$ | $n\text{-}C_4H_9OCH_2CH_2A$ | 179 | 0.5–0.65 | " |
| $n\text{-}C_{18}H_{37}OH$ | $n\text{-}C_{18}H_{37}OCH_2CH_2A$ | 108–110 | 0.0 | " |
| ammonia | $H_2NCH_2CH_2A$ | >250 | 0.0 | " |
| $CH_2{=}CH{-}CH_2NH_2$ | $CH_2{=}CH{-}CH_2NHCH_2CH_2A$ | 235–236 | 0.00–0.05 | colorless crystal, weakly basic |
| $n\text{-}C_3H_7NH_2$ | $n\text{-}C_3H_7NHCH_2CH_2A$ | 200–203 | 0.0–0.1 | " |
| $n\text{-}C_{12}H_{25}NH_2$ | $n\text{-}C_{12}H_{25}NHCH_2CH_2A$ | 124–125 | 0.1–0.2 | " |
| $n\text{-}C_{18}H_{37}NH_2$ | $n\text{-}C_{18}H_{37}NHCH_2CH_2A$ | 123–124 | 0.0–0.1 | " |
| $H_2NC_2H_4NH_2$ | $H_2NC_2H_4NHC_2H_4{-}A$ | 91–92 | 0.0 | " |
| $C_6H_5{-}NH_2$ (phenyl-$NH_2$) | $C_6H_5{-}NHCH_2CH_2A$ | 200–203 | 0.65–0.80 | " |
| o-$CH_3$-$C_6H_4$-$NH_2$ | o-$CH_3$-$C_6H_4$-$NHCH_2CH_2A$ | 148–150 | 0.50–0.65 | colorless crystal, neutral |
| m-$CH_3$-$C_6H_4$-$NH_2$ | m-$CH_3$-$C_6H_4$-$NHCH_2CH_2A$ | 127–130 | 0.35–0.55 | " |

TABLE 1-continued

| Active Hydrogen-Containing Compound Used | Synthesized 2-Substituted-4,6-Diamino-s-Triazine | | | |
|---|---|---|---|---|
| | Structural Formula | Melting Point (°C.) | Rf | State |
| $CH_3-\text{C}_6H_4-NH_2$ | $CH_3-\text{C}_6H_4-NHCH_2CH_2A$ | 125–130 | 0.38–0.58 | " |
| $C_6H_5-CH_2NH$ | $C_6H_5-CH_2-N(H)-CH_2CH_2A$ | 92–93 | 0.0–0.2 | " |
| 2-naphthyl-$NH_2$ | 2-naphthyl-$N(H)-CH_2CH_2A$ | 197–200 | 0.4–0.5 | " |
| $CH_3COOH$ | $CH_3COOCH_2CH_2A$ | 173 | 0.0 | " |
| thiazoline-C(Et)(NH)-C-SH | thiazoline-C(Et)(NH)-C(=S)-S-$CH_2CH_2A$ | 116–118 | 0.5–0.7 | lightly brown crystal, weakly acidic |
| 3-pyridyl-$NH_2$ | 3-pyridyl-$NHCH_2CH_2A$ | 240 | 0.4–0.5 | colorless crystal, slightly basic |
| benzotriazole-NH | benzotriazole-N-$CH_2CH_2A$ | 208–213 | 0.3–0.4 | colorless crystal, neutral |
| $HN(C_2H_4NH_2)_2$ | $HN(C_2H_4NHC_2H_4A)_2$ | 70–74 | 0.0 | colorless crystal, slightly basic |
| m-$C_6H_4(CH_2NH_2)_2$ | m-$C_6H_4(CH_2NHC_2H_4A)_2$ | 100–102 | 0.0 | colorless crystal, weakly basic |

EXAMPLE 1

A mixture comprising 0.1 mole of the 2-substituted-4,6-diamino-s-triazine synthesized according to the process described in the Referential Example, 0.1 mole of isocyanuric acid and a predetermined amount of an aqueous solvent was boiled for a predetermined time with stirring to completely dissolve the reactants, and the reaction mixture was cooled and the precipitated crystal was recovered by filtration and dried to obtain a corresponding adduct.

The kind of the used 2-substituted-4,6-diamino-s-triazine, the amount used of the solvent, the heating time and the yield of the adduct are shown in Table 2.

TABLE 2

| Used 2-Substituted-4,6-Diamino-s-Triazine | Amount (ml) of Solvent | Heating Time (minutes) | Amount (g) of Adduct | Yield (%) of Adduct |
|---|---|---|---|---|
| $CH_3OCH_2CH_2A$ | water, 2000 | 30 | 26.5 | 89 |
| n-$C_3H_7OCH_2CH_2A$ | water, 1290 | 180 | 32.6 | 100 |
| $(CH_3)_2CHOCH_2CH_2A$ | water, 2233 | 240 | 30.0 | 92 |
| n-$C_4H_9OCH_2CH_2A$ | water, 2000 | 40 | 21.1 | 62 |

TABLE 2-continued

| Used 2-Substituted-4,6-Diamino-s-Triazine | Amount (ml) of Solvent | Heating Time (minutes) | Amount (g) of Adduct | Yield (%) of Adduct |
|---|---|---|---|---|
| n-$C_{18}H_{37}OCH_2CH_2A$ | methanol, 500 | 60 | 38.4 | 72 |
| $H_2NCH_2CH_2A$ | water, 2000 | 30 | 22.9 | 81 |
| $CH_2$=CH—$CH_2NHCH_2CH_2A$ | water, 2000 | 20 | 22.6 | 70 |
| n-$C_3H_7NHC_2H_4A$ | water, 2000 | 30 | 24.2 | 75 |
| n-$C_{12}H_{25}NHCH_2CH_2A$ | methanol, 1000 | 30 | 36.3 | 80 |
| n-$C_{18}H_{37}NHCH_2CH_2A$ | methanol, 1000 | 60 | 43.9 | 82 |
| $H_2NC_2H_4NHC_2H_4A$ | water, 2000 | 20 | 21.8 | 67 |
| phenyl-$NHCH_2CH_2A$ | water, 2000 | 30 | 31.8 | 89 |
| 2-methylphenyl-$NHCH_2CH_2A$ | water, 40 and methanol, 40 | 5 | 32.1 | 86 |
| 3-methylphenyl-$NHCH_2CH_2A$ | water, 4000 | 240 | 28.3 | 76 |
| 4-methylphenyl-$NHCH_2CH_2A$ | water, 4000 | 180 | 24.2 | 65 |
| phenyl-$CH_2NHCH_2CH_2A$ | water, 2100 | 240 | 37.3 | 100 |
| 2-naphthyl-$NHCH_2CH_2A$ | water, 9000 | 120 | 39.3 | 96 |
| $CH_3COOCH_2CH_2A$ | water, 2000 | 20 | 21.5 | 66 |
| $CH_2$=$CHCOOCH_2CH_2A$ | water, 2000 | 20 | 26.8 | 79 |
| $CH_2$=$C(CH_3)$—$COOCH_2CH_2A$ | water, 2000 | 60 | 27.8 | 79 |
| (thiazoline derivative)—C-$SCH_2CH_2A$ | water, 2000 | 20 | 31.3 | 71 |
| 3-pyridyl-$NHCH_2CH_2A$ | water, 2000 | 30 | 21.2 | 59 |
| benzotriazolyl-$CH_2CH_2A$ | water, 2000 | 30 | 32.1 | 83 |
| $HN(C_2H_4NHC_2H_4A)_2$ | water, 3800 | 180 | 45.0 | 89 |

TABLE 2-continued

| Used 2-Substituted-4,6-Diamino-s-Triazine | Amount (ml) of Solvent | Heating Time (minutes) | Amount (g) of Adduct | Yield (%) of Adduct |
|---|---|---|---|---|
| 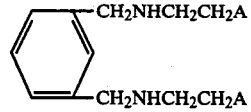—CH$_2$NHCH$_2$CH$_2$A, —CH$_2$NHCH$_2$CH$_2$A | water, 2000 | 20 | 38.5 | 71 |

EXAMPLE 2

A mixture of 0.1 mole of a 2-substituted-4,6-diamino-s-tirazine synthesized from a nitrile and dicyandiamide by a known reaction, 0.1 mole of isocyanuric acid and a predetermined amount of water was boiled for a predetermined time with stirring to completely dissolve the reactants, and the reaction mixture was cooled and the precipitated crystal was recovered by filtration and dried to obtain a corresponding adduct.

The kind of the used 2-substituted-4,6-diamino-s-triazine, the amount of water, the heating time and the yield of the adduct are shown in Table 3.

TABLE 3

| Used 2-Substituted-4,6 Diamino-s-Triazine | Amount (ml) of Water | Heating Time (minutes) | Amount (g) of Adduct | Yield (%) of Adduct |
|---|---|---|---|---|
| CH$_3$CH$_2$CH$_2$—A | 350 | 20 | 28.2 | 100 |
| n-C$_{17}$H$_{35}$—A | 2150 | 20 | 44.5 | 93 |
| 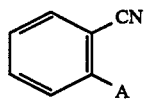 (CN, A) | 1060 | 10 | 31.0 | 91 |
| 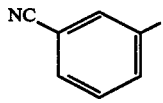 (NC, A) | 1060 | 10 | 28.3 | 83 |

TABLE 3-continued

| Used 2-Substituted-4,6 Diamino-s-Triazine | Amount (ml) of Water | Heating Time (minutes) | Amount (g) of Adduct | Yield (%) of Adduct |
|---|---|---|---|---|
| 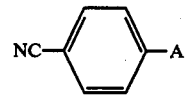 NC—⟨ ⟩—A | 2000 | 30 | 30.4 | 89 |

EXAMPLE 3

To 100 parts by weight of a polyepoxy resin (Epikote #828 supplied by Yuka-Shell Epoxy Co.) were added as indispensable components 15 parts by weight of a 2-substituted-4,6-diamino-s-triazine/isocyanuric acid adduct, 2.2 to 6.6 parts by weight of 2,4-diamino-6-(2′-methylimidazolyl-(1′))ethyl-s-triazine/isocyanuric acid adduct (Cuasol 2MAOK supplied by Shikoku Chemicals Corporation) and a viscosity adjusting agent (Aerosil #300 supplied by Nippon Aerosil Co.), and the mixture was blended by a three-roll mill to form a polyepoxy resin composition. The gel time of the composition at a temperature of 150° C. and the migration resistance of a coating formed by heating the composition at 150° C. for 15 minutes were determined.

The obtained results are shown in Table 4. The composition containing the adduct of the present invention showed a migration resistance of more than 1000 hours, but the composition free of the adduct of the present invention showed a migration resistance of less than 48 hours.

TABLE 4

| | Polyepoxy Resin Composition (parts) | | | | Properties of Cured Product | |
|---|---|---|---|---|---|---|
| Run No. | Epikote #828 | Cuasol 2MAOK | Aerosil #300 | Adduct or the Like | Hot Plate Method[1] Gel Time (seconds) | Migration Resistance (hours)[2] |
| 1 | 100 | 4.4 | 5 | CH$_3$CH$_2$—A/ICA,15 | 80 | more than 1000 |
| 2 | 100 | 4.4 | 5 | n-C$_{17}$H$_{35}$—A/ICA,15 | 98 | more than 1000 |
| 3 | 100 | 2.2 | 5 | CH$_3$O—CH$_2$CH$_2$—A/ICA,15 | 230 | more than 1000 |
| 4 | 100 | 4.4 | 5 | nC$_3$H$_7$OCH$_2$CH$_2$—A/ICA,15 | 90 | more than 1000 |
| 5 | 100 | 4.4 | 5 | (CH$_3$)$_2$CH—OCH$_2$CH$_2$—A/ICA,15 | 106 | more than 1000 |
| 6 | 100 | 4.4 | 5 | n-C$_4$H$_9$OCH$_2$CH$_2$—A/ICA,15 | 103 | more than 1000 |
| 7 | 100 | 6.6 | 5 | n-C$_{18}$H$_{37}$OCH$_2$CH$_2$—A/ICA,15 | 547 | more than 1000 |
| 8 | 100 | 4.4 | 5 | H$_2$NCH$_2$CH$_2$—A/ICA,15 | 90 | more than 1000 |
| 9 | 100 | 4.4 | 5 | CH$_2$=CHCH$_2$NH—CH$_2$CH$_2$—A/ICA,15 | 83 | more than 1000 |
| 10 | 100 | 4.4 | 5 | n-C$_3$H$_7$NHCH$_2$CH$_2$—A/ICA,15 | 80 | more than 1000 |
| 11 | 100 | 4.4 | 5 | nC$_{12}$H$_{25}$NHCH$_2$CH$_2$—A/ICA,15 | 80 | more than 1000 |
| 12 | 100 | 4.4 | 5 | nC$_{18}$H$_{37}$NHCH$_2$CH$_2$—A/ICA,15 | 80 | more than 1000 |
| 13 | 100 | 4.4 | 5 | 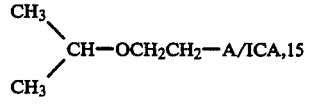 (CN, —A/ICA,15) | 129 | more than 1000 |

TABLE 4-continued

| | Polyepoxy Resin Composition (parts) | | | | Properties of Cured Product | |
|---|---|---|---|---|---|---|
| Run No. | Epikote #828 | Cuasol 2MAOK | Aerosil #300 | Adduct or the Like | Hot Plate Method[1] Gel Time (seconds) | Migration Resistance (hours)[2] |
| 14 | 100 | 4.4 | 5 | 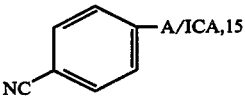 4-NC-C₆H₄-A/ICA,15 | 98 | more than 1000 |
| 15 | 100 | 4.4 | 5 | C₆H₅-NHCH₂CH₂-A/ICA,15 | 83 | more than 1000 |
| 16 | 100 | 4.4 | 5 | 3-CH₃-C₆H₄-NHCH₂CH₂-A/ICA,15 | 95 | more than 1000 |
| 17 | 100 | 4.4 | 5 | 4-CH₃-C₆H₄-NHCH₂CH₂-A/ICA,15 | 98 | more than 1000 |
| 18 | 100 | 4.4 | 5 | C₆H₅-CH₂NHCH₂CH₂-A/ICA,15 | 79 | more than 1000 |
| 19 | 100 | 4.4 | 5 | 2-naphthyl-NHCH₂CH₂-A/ICA,15 | 80 | more than 1000 |
| 20 | 100 | 2.2 | 5 | CH₃COOCH₂CH₂-A/ICA,15 | 490 | more than 1000 |
| 21 | 100 | 2.2 | 5 | CH₂=CHCOOCH₂CH₂-A/ICA,15 | 305 | more than 1000 |
| 22 | 100 | 4.4 | 5 | 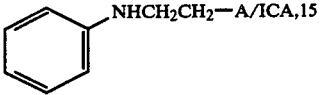 (imidazoline with C₂H₅, -C-SCH₂CH₂-A/ICA,15) | 73 | more than 1000 |
| 23 | 100 | 4.4 | 5 | 3-pyridyl-NHCH₂CH₂-A/ICA,15 | 67 | more than 1000 |
| 24 | 100 | 4.4 | 5 | benzotriazolyl-NCH₂CH₂-A/ICA,15 | 107 | more than 1000 |
| 25 | 100 | 4.4 | 5 | 1,3-C₆H₄(CH₂NHCH₂CH₂-A/ICA,15)₂ | 89 | more than 1000 |
| 26 | 100 | 4.4 | 5 | not added | 101 | 48 |
| 27 | 100 | 4.4 | 5 | CH₂=C(CH₃)-COOCH₂CH₂-A/ICA,15 | 127 | more than 1000 |

TABLE 4-continued

| Run No. | Polyepoxy Resin Composition (parts) | | | | Properties of Cured Product | |
|---|---|---|---|---|---|---|
| | Epikote #828 | Cuasol 2MAOK | Aerosil #300 | Adduct or the Like | Hot Plate Method[1] Gel Time (seconds) | Migration Resistance (hours)[2] |
| 28 | 100 | 4.4 | 5 | CH$_3$—CHCH$_2$NHCH$_2$CH$_2$—A/ICA,15<br>　　　　｜<br>　　　　OH | 90 | 5 |

Note
[1] About 0.3 g of the composition was placed on a hot plate maintained at a temperature of 150° C. and thinly expanded by a metal spatula, and the time required for bringing about the state where stringing was not caused between the spatula and the composition was measured.
[2] A copper-lined laminate according to G10 of NEMA Standard was etched to remove the copper foil, and a fan-shaped electrode circuit having a conductor interval of 0.5 mm was screen-printed with a silver powder/phenolic resin plate. The printed laminate was baked at 150° C. for 30 minutes. Then, the composition shown in Table 4 was screen-printed in a thickness of 20μ on the circuit and was then cured at 150° C. for 15 minutes to form a specimen.

A direct current voltage of 30 V was applied to the specimen and the specimen was allowed to stand still in an atmosphere maintained at a temperature of 60° C. and a relative humidity of 90 to 95%, and blackening of the anode with the lapse of time was checked.

EXAMPLE 4

A polyepoxy resin composition was prepared by uniformly mixing 100 parts by weight of a brominated epoxy resin (Epikote DX248B70 supplied by Yuka-Shell Epoxy Co.), 16 parts by weight of an equimolar mixture of 2-ethyl-4,6-diamino-s-triazine/isocyanuric acid adduct and Epikote #828, 0.78 part by weight of 2-ethyl-4-methylimidazole, 6.24 parts by weight of dicyandiamide and 83.7 parts by weight of methylcellosolve, and an aminosilane-treated glass fiber fabric having a thickness of 0.18 mm was impregnated with the composition. The solvent was removed by air drying to form a prepreg having a resin content of 39 to 44% by weight.

Eight prepregs prepared in the above-mentioned manner were piled and a copper foil having a thickness of 35μ was placed thereon, and the assembly was heat-pressed at 150° C. under a pressure of 50 kg/cm² for 60 minutes to effect curing. Then, post-curing was carried out at 180° C. for 60 minutes to form a copper-lined laminate.

For comparison, a polyepoxy resin composition comprising 100 parts by weight of Epikote DX248B70, 0.70 part by weight of 2-ethyl-4-methylimidazole, 5.4 parts by weight of dicyandiamide and 63.0 parts by weight of methylcellosolve was prepared, and by using this composition, a copper-lined laminate was prepared in the same manner as described above. The properties of both the copper-lined laminates were compared. The obtained results are shown in Table 5.

TABLE 5

| | Laminate Formed by Using Adduct-Incorporated Epoxy Resin | Laminate Formed by Using Adduct-Free Epoxy Resin |
|---|---|---|
| Copper Foil Peel Strength (Kg/cm)[1] | 1.8 | 1.8 |
| Flame-out Property (seconds)[2] | 3.56 (0.8–7.0) | 2.4 (0.5–4.0) |
| Migration Resistance[3] | no change for 1000 hours | blackening of anode after 300 hours |

Note
[1] The strength measured when the copper foil was peeled from the copper-lined laminate having a width of 10 mm at a speed of 5 mm/min in the vertical direction.
[2] Measured according to the vertical method of UL-94 (parenthesized values are those of 10 specimens)
[3] The same as described above.

EXAMPLE 5

Copper foils of a paper-phenolic laminate and a glass-epoxy laminate were etched to form circuits. An adduct-containing, electrically conductive silver paste and an adduct-free, electrically conductive silver paste were independently screen-printed to form fan-shaped electrodes at a conductor interval of 0.5 mm, followed by baking at 150° C. for 30 minutes. An overcoat epoxy resin comprising the following ingredients was screen-printed in a thickness of 20μ on each circuit. The coated circuit was heated at 150° C. for 30 minutes to effect curing and from a specimen. A direct current voltage of 30 V was applied to the specimen, and the specimen was allowed to stand still in an atmosphere maintained at a temperature of 60° C. and a relative humidity of 90 to 95%. Blackening of the anode with the lapse of time was checked. The obtained results are shown in Table 6.

| Overcoat Epoxy Resin Composition | |
|---|---|
| Epikote #828 (supplied by Yuka-Shell Epoxy Co.) | 100 parts by weight |
| 2,4-Diamino-6-(2'-methylimidazolyl-(1'))-2-ethyl-4,6-diamino-s-triazine/isocyanuric acid adduct | 6 parts by weight |
| Dicyandiamide | 2 parts by weight |
| Barium sulfate | 83 parts by weight |
| Phthalocyanine Green | 2 parts by weight |
| Swasol (supplied by Maruzen Sekiyu Co.) | 3.5 parts by weight |
| Xylene | 0.3 part by weight |
| Isopropyl alcohol | 0.05 part by weight |

TABLE 6

| | Run No. | | | | |
|---|---|---|---|---|---|
| | 1 | 2 | 3 | 4 | 5 |
| Composition of Paste | | | | | |
| Binder for paste[1] | 17.2 | 17.2 | 17.2 | 17.2 | 17.2 |
| Silver powder | 77.4 | 77.4 | 77.4 | 77.4 | 77.4 |
| Butylcarbitol acetate | 5.4 | 5.4 | 5.4 | 5.4 | 5.4 |
| CH$_3$CH$_2$—A/ICA | 15 | | | | |
| CH$_2$=CHCOOCH$_2$CH$_2$—A/ICA | | 15 | | | |

TABLE 6-continued

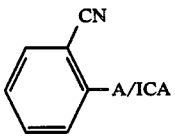

| | 1 | 2 | 3 | 4 | 5 |
|---|---|---|---|---|---|
| | | | | | 15 |
| $CH_2=C(CH_3)COOCH_2-CH_2-A/ICA$ | | | 15 | | 15 |
| Test Results | | | | | |
| Migration Resistance (hours)[2] | | | | | |
| Paper-phenolic laminate | more than 5 | more than 24 | more than 17 | less than 5 | more than 24 |
| Glass-epoxy laminate | more than 5 | more than 5 | more than 5 | less than 5 | more than 5 |

Note
[1]The composition of the binder was as follows.

| | |
|---|---|
| Epikote #838 | 100 parts by weight |
| EOCN102S-CS (supplied by Nippon Kayaku Co.) | 233.4 parts by weight |
| Resin M (supplied by Maruzen Sekiyu Co.) | 111.1 parts by weight |
| Antifoamer KS603 (supplied by Shinetsu Silicone Co.) | 2.4 parts by weight |
| 2,4-Diamino-6-(2'-methylimi-dazolyl-(1'))-2-ethyl-4,6-diamino-s-triazine/isocyanuric acid adduct | 7.3 parts by weight |
| Xylene resin | 37.1 parts by weight |
| Butylcellosolve acetate | 111.1 parts by weight |

[2]The same as described above.

EXAMPLE 6

An undercoating agent containing the adduct and an undercoating agent free of the adduct were independently screen-printed in a thickness of $20\mu$ on non-copper-foil-lined surfaces of paper-phenolic laminates, and the laminates were heated at 150° C. for 30 minutes to effect curing. Then, an electrically conductive silver paste comprising the same adduct as used for the undercoating agent (comprising 17.2 parts by weight of the same paste binder as described above, 77.4 parts by weight of silver powder, 5.4 parts by weight of butylcarbitol acetate and 15 parts by weight of the adduct) or an electrically conductive silver paste free of the adduct (comprising 17.2 parts by weight of the same paste binder as described above, 77.4 parts by weight of silver powder and 5.4 parts by weight of butylcarbitol acetate) was screen-printed to form a fan-shaped electrode at a conductor interval of 0.5 mm, followed by baking at 150° C. for 30 minutes. Then, the same overcoat epoxy resin composition as used in Example 5 was screen-printed in a thickness of $20\mu$ on the circuit and baked at 150° C. for 30 minutes to effect curing and form a specimen. A direct current voltage of 30 V was applied to the specimen, and the specimen was allowed to sand still in an atmosphere maintained at a temperature of 60° C. and a relative humidity of 90 to 95%. Blackening of the anode with the lapse of time was checked. The obtained results are shown in Table 7.

TABLE 7

| | Run No. | | | | |
|---|---|---|---|---|---|
| | 1 | 2 | 3 | 4 | 5 |
| Composition (parts by weight) of Undercoating Agent | | | | | |
| Epikote #828 | 100 | 100 | 100 | 100 | 100 |
| Cuasol 2MAOK | 4.4 | 4.4 | 4.4 | 4.4 | 4.4 |
| Aerosil #300 | 5 | 5 | 5 | 5 | 5 |
| $CH_3CH_2-A/ICA$ | 15 | | | | |
| $n-C_{17}H_{35}-A/ICA$ | | 15 | | | |
| $CH_2=CHCOOCH_2CH_2A/ICA$ | | | 15 | | |
| $CH_2=C(CH_3)COOCH_2CH_2A/ICA$ | | | | | 15 |

TABLE 7-continued

| | Run No. | | | | |
|---|---|---|---|---|---|
| | 1 | 2 | 3 | 4 | 5 |
| ICA | | | | | |
| Test Results | | | | | |
| Migration Resistance (hours)[1] | more than 48 | more than 24 | more than 60 | less than 15 | more than 60 |

Note
[1]The same as described above.

EXAMPLE 7

With respect to each of silver electrode/silver electrode comprising an intermediate layer of an epoxy resin containing or not containing the adduct and silver electrode/copper electrode comprising an intermediate layer of the same epoxy resin, changes of insulation resistances were measured under application of a direct current voltage of 50 V in an atmosphere maintained at a temperature of 60° C. and a relative humidity of 90 to 95%.

In case of silver electrode/silver electrode, a silver-phenolic resin type silver conductor was screen-printed on a non-copper-foil-lined surface of a paper-phenolic laminate and was baked at 150° C. for 30 minutes to form an electrode. Then, a composition shown in Table 8 was screen-printed in a thickness of $30\mu$ on the electrode and baked at 150° C. for 30 minutes, and the same silver conductor as described above was applied thereon and the same composition as described above was screen-printed in a thickness of 30 $\mu$ on the silver conductor to form a sample. In case of silver electrode/copper electrode, the copper foil of a paper-phenolic laminate was etched to form one electrode and the other electrode was formed in the same manner as described above with respect to silver electrode/silver electrode.

The obtained results are shown in Table 8.

TABLE 8

|  | Run No. | | | |
| --- | --- | --- | --- | --- |
|  | 1 | 2 | 3 | 4 |
| Epoxy Resin Composition (parts by weight) | | | | |
| Epikote #828 | 100 | 100 | 100 | 100 |
| Cuasol 2MAOK | 7 | 7 | 7 | 7 |
| Dicyandiamide | 4 | 4 | 4 | 4 |
| Silane coupling agent | 0.3 | 0.3 | 0.3 | 0.3 |
| Talc | 20 | 20 | 20 | 20 |
| Barium sulfate | 60 | 60 | 60 | 60 |
| $CH_3OCH_2CH_2$—A/ICA | 10 | | | |
| $CH_2$=$CHCOOCH_2CH_2$A/ICA | | 10 | | |
| $n-C_{17}H_{35}$—A/ICA | | | 10 | |
| Test Results | | | | |
| Migration Resistance (hours)[1] | | | | |
| silver/silver | more than 300 | more than 300 | more than 300 | less than 100 |
| silver/copper | more than 300 | more than 300 | more than 300 | less than 100 |

Note
[1] The time required for reducing the insulation resistance from the initial value ($10^{13}$ Ω) to a level lower than $10^8$ Ω was measured.

We claim:
1. A 2-substituted-4,6-diamino-s-triazine/isocyanuric acid adduct represented by the following formula:

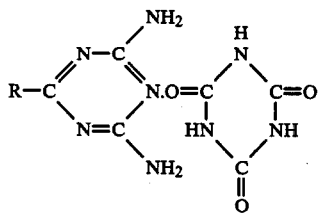

wherein R stands for an alkyl group having 2 to 20 carbon atoms, an unsubstituted or cyano group-substituted aryl group, or a group of the formula $R^1$—$CH_2CH_2$— in which $R^1$ stands for an alkoxy group having up to 20 carbon atoms, an acyloxy group, an amino group, an N-substituted amino group, a benzotriazolyl group or a 2-alkylimidazolyl-(4)-dithiocarbonyl group, or by the following formula:

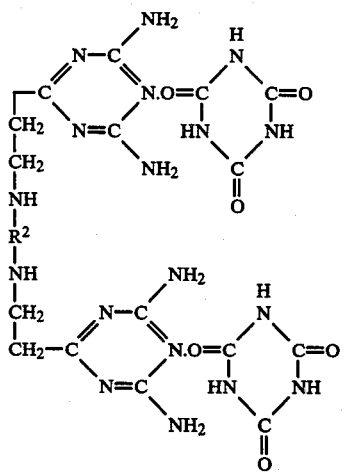

wherein $R^2$ stands for an alkylene group which may have an intervening imino or phenylene group.

2. An adduct as set forth in claim 1, wherein R stands for an alkyl group selected from the group consisting of an ethyl group, an n-propyl group and an n-heptadecyl group.

3. An adduct as set forth in claim 1, wherein R stands for a cyanoaryl group selected from the group consisting of o-, m- and p-cyanophenyl groups.

4. An adduct as set forth in claim 1, which is represented by the following formula:

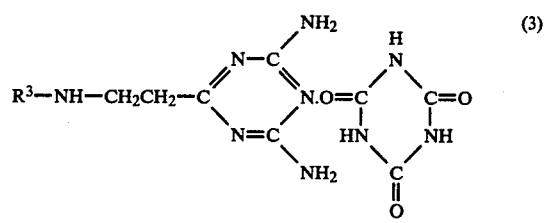

wherein $R^3$ stands for a hydrogen atom, a monovalent hydrocarbon group having up to 18 carbon atoms, an aminoalkyl group, a monovalent heterocyclic group or an acyl group.

5. An adduct as set forth in claim 4, wherein the monovalent hydrocarbon group is an alkyl group, an alkenyl group, an aralkyl group, an alkaryl group or an aryl group.

6. An adduct as set forth in claim 4, wherein the monovalent heterocyclic group is a pyridyl group.

7. An adduct as set forth in claim 4, wherein the acyl group is an acyl group derived from a saturated or unsaturated carboxylic acid.

8. An adduct as set forth in claim 1, wherein the acyloxy group is an acyloxy group derived from a saturated or unsaturated carboxylic acid.

9. An adduct as set forth in claim 1, which is 2-ethyl-4,6-diamino-s-triazine/isocyanuric acid adduct.

10. An adduct as set forth in claim 1, which is 2-n-propyl-4,6-diamino-s-triazine/isocyanuric acid adduct.

11. An adduct as set forth in claim 1, which is 2-heptadecyl-4,6-diamino-s-triazine/isocyanuric acid adduct.

12. An adduct as set forth in claim 1, which is 2-methoxyethyl-4,6-diamino-s-triazine/isocyanuric acid adduct.

13. An adduct as set forth in claim 1, which is 2-n-propoxyethyl-4,6-diamino-s-triazine/isocyanuric acid adduct.

14. An adduct as set forth in claim 1, which is 2-isopropoxyethyl-4,6-diamino-s-triazine/isocyanuric acid adduct.

15. An adduct as set forth in claim 1, which is 2-n-butoxyethyl-4,6-diamino-s-triazine/isocyanuric acid adduct.

16. An adduct as set forth in claim 1, which is 2-n-octadecyloxyethyl-4,6-diamino-s-triazine/isocyanuric acid adduct.

17. An adduct as set forth in claim 1, which is 2-aminoethyl-4,6-diamino-s-triazine/isocyanuric acid adduct.

18. An adduct as set forth in claim 1, which is 2-allylaminoethyl-4,6-diamino-s-triazine/isocyanuric acid adduct.

19. An adduct as set forth in claim 1, which is 2-propylaminoethyl-4,6-diamino-s-triazine/isocyanuric acid adduct.

20. An adduct as set forth in claim 1, which is 2-n-dodecylaminoethyl-4,6-diamino-s-triazine/isocyanuric acid adduct.

21. An adduct as set forth in claim 1, which is 2-octadecylaminoethyl-4,6-diamino-s-triazine/isocyanuric acid adduct.

22. An adduct as set forth in claim 1, which is 2-aminoethylaminoethyl-4,6-diamino-s-triazine/isocyanuric acid adduct.

23. An adduct as set forth in claim 1, which is 2-o-cyanophenyl-4,6-diamino-s-triazine/isocyanuric acid adduct.

24. An adduct as set forth in claim 1, which is 2-m-cyanophenyl-4,6-diamino-s-triazine/isocyanuric acid adduct.

25. An adduct as set forth in claim 1, which is 2-p-cyanophenyl-4,6-diamino-s-triazine/isocyanuric acid adduct.

26. An adduct as set forth in claim 1, which is 2-phenylaminoethyl-4,6-diamino-s-triazine/isocyanuric acid adduct.

27. An adduct as set forth in claim 1, which is 2-o-toluylaminoethyl-4,6-diamino-s-triazine/isocyanuric acid adduct.

28. An adduct as set forth in claim 1, which is 2-m-toluylaminoethyl-4,6-diamino-s-triazine/isocyanuric acid adduct.

29. An adduct as set forth in claim 1, which is 2-p-toluylaminoethyl-4,6-diamino-s-triazine/isocyanuric acid adduct.

30. An adduct as set forth in claim 1, which is 2-benzylaminoethyl-4,6-diamino-s-triazine/isocyanuric acid adduct.

31. An adduct as set forth in claim 1, which is 2-β-naphthylaminoethyl-4,6-diamino-s-triazine/isocyanuric acid adduct.

32. An adduct as set forth in claim 1, which is 2-acetoxyethyl-4,6-diamino-s-triazine/isocyanuric acid adduct.

33. An adduct as set forth in claim 1, which is 2-acryloyloxyethyl-4,6-diamino-s-triazine/isocyanuric acid adduct.

34. An adduct as set forth in claim 1, which is 2-methacryloyloxyethyl-4,6-diamino-s-triazine/isocyanuric acid adduct.

35. An adduct as set forth in claim 1, which is 2-(2'-ethylimidazolyl-(4))-dithiocarbonylethyl-4,6-diamino-s-triazine/isocyanuric acid adduct.

36. An adduct as set forth in claim 1, which is 2-β-pyridylaminoethyl-4,6-diamino-s-triazine/isocyanuric acid adduct.

37. An adduct as set forth in claim 1, which is 2-benzotriazolyethyl-4,6-diamino-s-triazine/isocyanuric acid adduct.

38. An adduct as set forth in claim 1, which is 2-(bis-1',3'-diethylene-triaminoethyl)-4,6-diamino-s-triazine/isocyanuric acid adduct.

39. An adduct as set forth in claim 1, which is 2-(bis-m-xylylene-diaminoethyl)-4,6-diamino-s-triazine/isocyanuric acid adduct.

40. A process for the synthesis for 2-substituted-4,6-diamino-s-triazine/isocyanuric acid adducts, which comprises heating and dissolving a 2-substituted-4,6-diamino-s-triazine represented by the following formula:

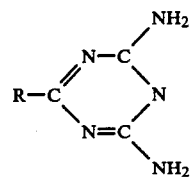

wherein R stands for an alkyl group having 2 to 20 carbon atoms, an unsubstituted or cyano group-substituted aryl group, or a group of the formula $R^1$—$CH_2CH_2$— in which $R^1$ stands for an alkoxy group having up to 20 carbon atoms, an acyloxy group, an amino group, an N-substituted amino group, a benzotriazolyl group or a 2-alkylimidazolyl-(4)-dithiocarbonyl group, or by the following formula:

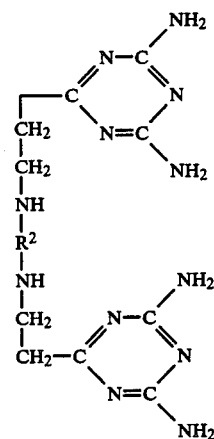

wherein $R^2$ stands for an alkylene group which may have an intervening imino or phenylene group, and an equimolar or substantially equimolar amount of isocyanuric acid in the presence of water, cooling the reaction mixture, recovering the precipitated crystal, and drying the crystal.

41. A curing agent for an epoxy resin, which comprises a 2-substituted-4,6-diamino-s-triazine/isocyanuric acid adduct as set forth in claim 1.

42. A process for curing polyepoxy resins, which comprises mixing 100 parts by weight of an epoxy resin with 5 to 50 parts by weight of a 2-substituted-4,6-diamino-s-triazine/isocyanuric acid adduct represented by the following formula:

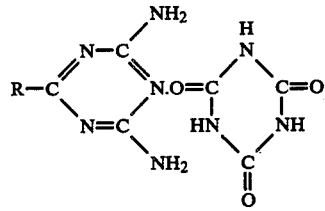

wherein R stands for an alkyl group having 2 to 20 carbon atoms, an unsubstituted or cyano group-substituted aryl group, or a group of the formula $R^1$—$CH_2CH_2$— in which $R^1$ stands for an alkoxy group having up to 20 carbon atoms, an acyloxy group, an amino group, an N-substituted amino group, a benzotriazolyl group or a 2-alkylimidazolyl-(4)-dithiocarbonyl group, or by the following formula:

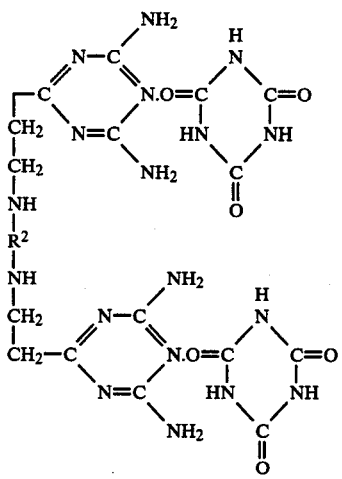

(2)

wherein $R^2$ stands for an alkylene group which may have an intervening imino or phenylene group, and 0.025 to 10 parts by weight of a curing agent selected from the group consisting of aliphatic amines, aromatic amines, tertiary amines, polyamide resins and acid anhydrides, and heating the mixture.

43. A process for curing polyepoxy resins, which comprises mixing 100 parts by weight of an epoxy resin with 5 to 50 parts by weight of a 2-substituted-4,6-diamino-s-triazine/isocyanuric acid adduct represented by the following formula:

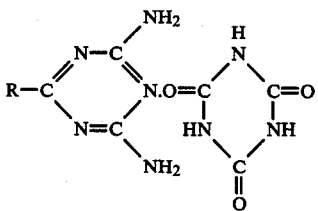

(1)

wherein R stands for an alkyl group having 2 to 20 carbon atoms, an unsubstitued or cyano group-substituted aryl group, or a group of the formula $R^1—CH_2CH_2—$ in which $R^1$ stands for an alkoxy group having up to 20 carbon atoms, an acyloxy group, an amino group, an N-substituted amino group, a benzotriazolyl group or a 2-alkylimidazolyl-(4)-dithiocarbonyl group, or by the following formula:

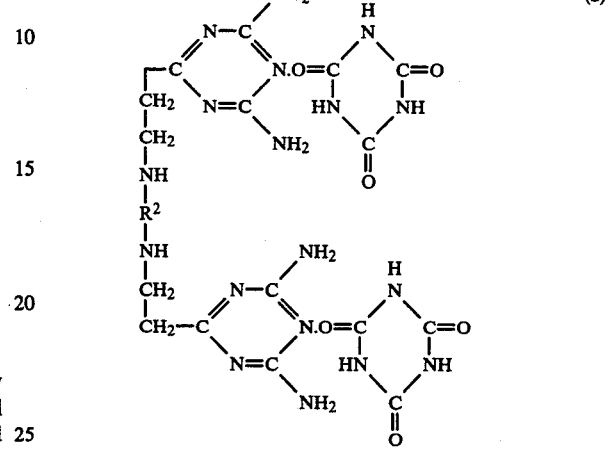

(2)

wherein $R^2$ stands for an alkylene group which may have an intervening imino or phenylene group, and 0.025 to 10 parts by weight of at least one imidazole compound selected from the group consisting of 2,4-diamino-(2'-methylimidazolyl-(1'))ethyl-s-triazine, 2,4-diamino-6-(2'-methylimidazolyl-(1'))ethyl-s-triazine/isocyanuric acid adduct, 2-phenyl-4,5-dihydroxymethylimidazole, 2-phenyl-4-methyl-5-hydroxymethylimidazole, 4,4'-methylene-bis-(2-ethyl-5-methylimidazole), 2-phenyl-4-benzyl-5-hydroxymethylimidazole, 2-phenyl-4,5-dibenzylimidazole, 2-methylimidazole, 2-ethyl-4-methylimidazole, 2-phenylimidazole, 2-undecylimidazole, 2-heptadecylimidazole, 2-phenyl-4-methylimidazole, 1-cyanoethyl-2-methylimidazole, 1-cyanoethyl-2-ethyl-4-methylimidazole, 1-cyanoethyl-2-undecylimidazole, 1-cyanoethyl-2-phenyl-4-methylimidazole and 1-benzyl-2-methylimidazole, and heating the mixture.

* * * * *